(12) United States Patent
O'Rourke

(10) Patent No.: US 11,166,643 B2
(45) Date of Patent: Nov. 9, 2021

(54) NON-INVASIVE METHOD OF ESTIMATING INTRA-CRANIAL PRESSURE (ICP)

(71) Applicant: Michael F. O'Rourke, Hunters Hill (AU)

(72) Inventor: Michael F. O'Rourke, Hunters Hill (AU)

( * ) Notice: Subject to any disclaimer, the term of this patent is extended or adjusted under 35 U.S.C. 154(b) by 828 days.

(21) Appl. No.: 15/614,232

(22) Filed: Jun. 5, 2017

(65) Prior Publication Data
US 2017/0360318 A1 Dec. 21, 2017

(30) Foreign Application Priority Data
Jun. 7, 2016 (AU) .................................. 2016902207

(51) Int. Cl.
| | |
|---|---|
| *A61B 5/00* | (2006.01) |
| *A61B 5/03* | (2006.01) |
| *A61B 5/022* | (2006.01) |
| *A61B 5/026* | (2006.01) |
| *A61B 8/08* | (2006.01) |

(52) U.S. Cl.
CPC .............. *A61B 5/031* (2013.01); *A61B 5/022* (2013.01); *A61B 5/026* (2013.01); *A61B 5/4064* (2013.01); *A61B 5/6822* (2013.01); *A61B 5/6824* (2013.01); *A61B 5/7239* (2013.01); *A61B 5/7257* (2013.01); *A61B 5/7278* (2013.01); *A61B 8/488* (2013.01); *A61B 2505/01* (2013.01)

(58) Field of Classification Search
CPC ....... A61B 5/031; A61B 5/4064; A61B 5/024; A61B 5/021; G16H 50/30; A61M 2230/04; A61M 2205/3331; A61N 1/0534
USPC ....... 600/300, 561, 558, 559, 483, 485, 490; 128/920; 33/511, 512
See application file for complete search history.

(56) References Cited

U.S. PATENT DOCUMENTS

| | | | | |
|---|---|---|---|---|
| 5,265,011 A | * | 11/1993 | O'Rourke | A61B 5/021 128/920 |
| 5,617,873 A | * | 4/1997 | Yost | A61B 5/031 33/511 |
| 6,117,089 A | * | 9/2000 | Sinha | A61B 5/031 600/561 |

(Continued)

*Primary Examiner* — May A Abouelela
(74) *Attorney, Agent, or Firm* — Stoel Rives LLP

(57) ABSTRACT

A non-invasive method of estimating intra-cranial pressure (ICP). The method including the steps of: a. non-invasively measuring pressure pulses in an upper body artery; b. determining central aortic pressure (CAP) pulses that correspond to these measured pressure pulses; c. identifying features of the ICP wave which denote cardiac ejection and wave reflection from the cranium, including Ejection Duration (ED) and Augmentation Index of Pressure (PAIx); d. non-invasively measuring flow pulses in a central artery which supplies blood to the brain within the cranium; e. identifying features of the measured cerebral flow waves which denote cardiac ejection and wave reflection from the cranium as Flow Augmentation Index (FAIx); f. calculating an ICP flow augmentation index from the measured central flow pulses; g. comparing the calculated ICP pressure augmentation index (PAIx) and flow augmentation index (FAIx) to measure (gender-specific) pressure and flow augmentation data indicative of a measured ICP to thereby estimate actual ICP; and h. noting any disparity between ED measured for pressure waves and ED measured for flow.

13 Claims, 7 Drawing Sheets

(56) References Cited

U.S. PATENT DOCUMENTS

| | | | | |
|---|---|---|---|---|
| 6,146,336 A * | 11/2000 | Paulat | A61B 5/0205 | 600/547 |
| 6,231,509 B1 * | 5/2001 | Johnson | A61B 5/031 | 600/438 |
| 6,558,336 B2 * | 5/2003 | Collins | A61B 5/031 | 600/301 |
| 6,589,189 B2 * | 7/2003 | Meyerson | A61B 5/031 | 600/559 |
| 6,976,963 B2 * | 12/2005 | Clift | A61B 5/0205 | 600/483 |
| 7,147,605 B2 * | 12/2006 | Ragauskas | A61B 5/031 | 600/561 |
| 8,157,730 B2 * | 4/2012 | LeBoeuf | A61B 5/6815 | 600/300 |
| 8,216,140 B2 * | 7/2012 | Gur | A61B 3/16 | 600/401 |
| 8,343,062 B2 * | 1/2013 | Fortin | A61B 5/0059 | 600/479 |
| 8,632,475 B2 * | 1/2014 | Stone | A61B 5/031 | 600/559 |
| 8,998,818 B2 * | 4/2015 | Pranevicius | A61B 5/02108 | 600/419 |
| 9,138,154 B2 * | 9/2015 | Weinberg | A61B 5/031 | |
| 9,433,358 B2 * | 9/2016 | Lowe | A61B 5/021 | |
| 10,149,624 B2 * | 12/2018 | Kuenen | A61B 5/031 | |
| 2001/0027335 A1 * | 10/2001 | Meyerson | A61B 5/031 | 607/116 |
| 2007/0123796 A1 * | 5/2007 | Lenhardt | A61B 8/0808 | 600/561 |
| 2007/0287899 A1 * | 12/2007 | Poupko | A61B 5/026 | 600/383 |
| 2008/0015421 A1 * | 1/2008 | Penner | A61N 1/37217 | 600/300 |
| 2008/0064968 A1 * | 3/2008 | Martin | A61B 5/0048 | 600/493 |
| 2008/0077023 A1 * | 3/2008 | Campbell | A61B 5/0205 | 600/502 |
| 2009/0062625 A1 * | 3/2009 | Eide | A61B 5/021 | 600/300 |
| 2010/0137736 A1 * | 6/2010 | Addington | A61M 15/00 | 600/546 |
| 2010/0152608 A1 * | 6/2010 | Hatlestad | A61B 5/0028 | 600/561 |
| 2011/0201962 A1 * | 8/2011 | Grudic | A61B 5/021 | 600/561 |
| 2012/0197088 A1 * | 8/2012 | Karamanoglu | A61B 5/02116 | 600/300 |
| 2013/0197390 A1 * | 8/2013 | Weinberg | A61B 5/0205 | 600/561 |
| 2014/0235960 A1 * | 8/2014 | Addington | A61J 15/0049 | 600/301 |
| 2014/0316288 A1 * | 10/2014 | Chowienczyk | A61B 5/02108 | 600/485 |
| 2014/0350348 A1 * | 11/2014 | Tee | A61B 5/0002 | 600/300 |
| 2015/0359448 A1 * | 12/2015 | Beach | A61B 8/15 | 600/301 |

* cited by examiner

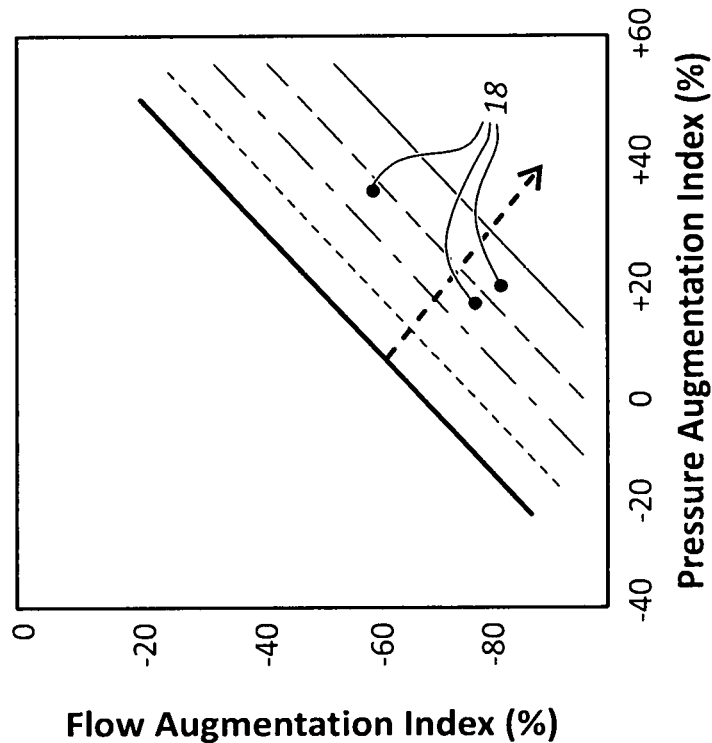
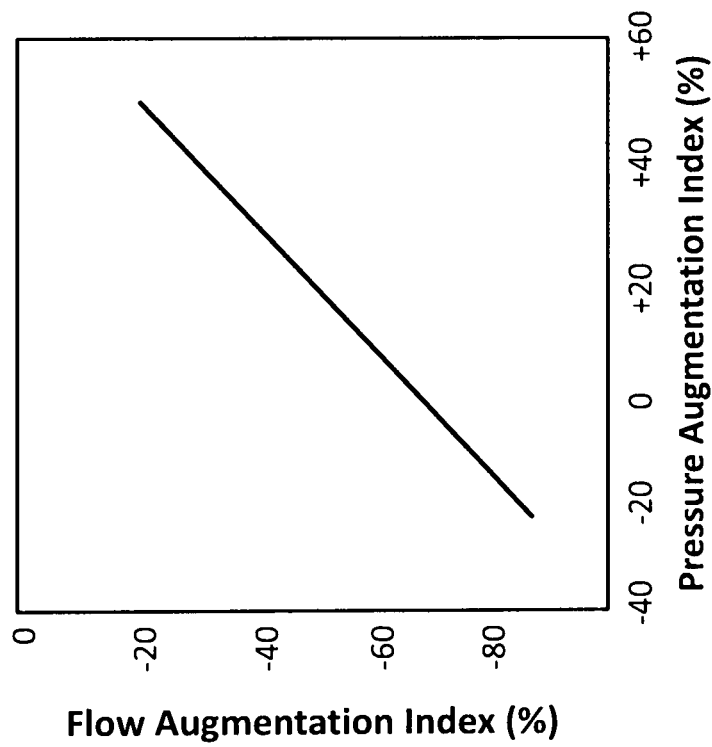
FIG. 3B
FIG. 3A

NON-INVASIVE METHOD OF ESTIMATING INTRA-CRANIAL PRESSURE (ICP)

CROSS-REFERENCE TO RELATED APPLICATIONS

This application claims priority to Australian Provisional Patent Application No. 7016902207, filed on Jun. 7, 2016, which is hereby incorporated by reference in its entirety.

FIELD OF THE INVENTION

The present invention relates a non-invasive method of estimating intra-cranial pressure (ICP).

BACKGROUND OF THE INVENTION

The cranium is the bony vault at the top of the human body which contains the body's computer, the brain (FIG. 1). The cranial cavity communicates directly with the spinal canal. This contains the spinal cord wherein nerve pathways from and to the brain pass before entering canals between the vertebrae and the rest of the body. Despite allowing free passage of electrical signals in the insulated nerves from brain to body, the combined cranial cavity and spinal canal are physically isolated from the rest of the body because foramena in the cranium and spine are physically plugged with connective tissue. This "plugging" prevents leakage of the Cerebro-Spinal Fluid (CSF) which surrounds and bathes the brain and spinal cord within the cranial cavity and spinal canal. The only physical passage between the conjoined cranial cavity/spinal canal and the rest of the body is for the major arteries and veins (notably the internal carotid artery and vertebral artery on each side of the body, and the jugular veins on each side).

This physical arrangement of brain and spinal cord protects these fragile vital organs from trauma and provides a physical syphon which helps to maintain blood flow to the brain with different body positions, particularly when adopting the upright stance. A particular problem with trauma or disease, especially brain swelling from cerebral oedema, brain tumor or bleeding or interference with CSF circulation or absorption, is rise in ICP. Rise in ICP compresses and narrows cerebral arteries and veins in the cranium and restricts cerebral flow and can cause cerebral ischemia and secondary stroke. Elevation of ICP can also, through pressure on vital brain stem centers, increase autonomic nerve activity, with sympathetic nerve discharge elevating blood pressure in the general systemic circulation.

Current methods of measuring ICP are all invasive in nature. For example, ICP can be measured directly from the cerebral ventricle through a fluid-filled catheter attached to an external monitor. ICP can also be measured and monitored by inserting a needle between lumbar vertebrae into the dural sac which contains the spinal curd (i.e. by lumbar puncture), and measuring pressure by an external manometer. The most common current procedure in neurosurgical critical care is the insertion of a Codman (or similar) micromanometer through a hole drilled though the skull and advanced into the cerebral ventricle or into the cerebral parenchyma.

Direct (i.e. invasive) continuous measurement of ICP has become routine in most major neurosurgical units which deal with brain trauma, and is accompanied by direct continuous measurement of pressure waves from the radial artery by indwelling cannula. Monitoring is usually continued for the first few days after trauma or stroke, when elevations of ICP are most common, most amenable to treatment, and most likely to aid recovery.

Direct (i.e. invasive) measurement of ICP carries procedural risk of cerebral damage, haemorrhage and infection. While attempts have been made, there are no accepted methods for measuring ICP non-invasively. More particularly, current non-invasive or minimally invasive methods, which depend on the most readily available measures (arterial pressure and/or intra-cerebral blood flow), have not been successful in elucidating presence or absence of elevated ICP, nor gauging the degree of elevation in unconscious patients following closed head trauma, stroke or brain surgery.

Ability to measure ICP non-invasively can avoid the complications of direct ICP monitoring, where a pressure sensor is inserted into the brain parenchyma or into a cerebral ventricle. This is a routine procedure for severe closed head injury cases, in whom elevation of ICP can be relieved physically by withdrawal of CSF or by craniectomy (brain decompression). Complications include further brain injury, bleeding, infection. A method for measuring ICP quickly and non-invasively would shorten the delay between injury and decompression so improving the chance of a successful outcome, in head injury patients.

Ability to measure ICP can also help to establish a diagnosis of brain death in a potential transplant donor, and so improve chances of successful recipient organ transplantation.

OBJECT OF THE INVENTION

It is an object of the present invention to substantially overcome or at least ameliorate one or more of the above disadvantages, while preserving accuracy of the invasive method, and provide other advantages that arise from measurement of central rather than peripheral pressure, and central blood flow into and out from the cranium during the cardiac cycle.

SUMMARY OF THE INVENTION

The applicant contends that elevation of ICP can be estimated from the patterns of arterial pressure and flow waves which pass into the cranium to supply blood to the brain, and arise as a consequence of arterial narrowing and occlusion.

The applicant further contends that elevation and degree of elevation of ICP can be estimated from the patterns of pressure and flow waves in arteries (typically the carotid arteries and their major branches in the cranium) which enter the cranium to supply blood to the brain, as a consequence of their compression and narrowing on entry into the cranial cavity. The thesis is also based on change in the pattern of pressure and flow waves immediately upstream from their entry into the cranium where a site of very low wave reflection (approximating zero) changes progressively to a site of very high wave reflection (approaching 100%) when ICP rises to levels close to those seen in the peripheral circulation. Under these circumstances there is predisposition to appearance of "resonance" or "standing waves" in the general systemic circulation at a particular frequency.

Accordingly, in a first aspect, the present invention provides a non-invasive method of estimating intra-cranial pressure (ICP), the method including the steps of:

a. non-invasively measuring pressure pulses in an upper body artery;
b. determining a central arterial pressure (CAP) pulse waveform that corresponds to these measured pressure pulses;
c. identifying features of the central arterial pressure pulse waveform (CAP) which denote cardiac ejection and wave reflection from the cranium, including ejection duration (ED) and pressure augmentation index (PAIx);
d. non-invasively measuring flow pulses in a central artery which supplies blood to the brain within the cranium;
e. determining a central flow pulse waveform that corresponds to the measured flow pulses;
f. identifying features of the measured cerebral flow waves which denote cardiac ejection and wave reflection from the cranium, including flow augmentation index (FAIx);
g. comparing the calculated pressure augmentation index (PAIx) and flow augmentation index (FAIx) to (gender-specific) pressure and flow augmentation data indicative of a measured ICP to thereby estimate actual ICP; and
h. noting any disparity between ED measured for pressure waves and ED measured for flow as an indication of elevated ICP.

In one form, step a. includes measuring peripheral (radial) pressure pulses in a peripheral artery. In this form, step b. includes determining a peripheral pressure pulse waveform from the measured peripheral pulses and calculating the corresponding central pressure pulse waveform from the peripheral pressure pulse waveform, most preferably by using a transfer function. The peripheral pressure pulses are preferably measured in the radial artery at the wrist, non-invasively or invasively if a monitoring catheter is already in use.

In an alternative form, step a. includes measuring carotid pressure pulses in a carotid artery. In this alternative form, step b. includes measuring the corresponding central pressure pulses, for example by applanation tonometry.

The flow pulses in step c. are preferably measured in an upper body artery which supplies blood to the brain, such as the internal carotid artery, anterior cerebral artery, middle cerebral artery or common carotid artery.

In a second aspect, the present invention provides a non-invasive method of estimating intra-cranial pressure (ICP), the method including the steps of:
a. non-invasively measuring pressure pulses in an upper body artery;
b. determining a central pressure pulse waveform that corresponds to the measured pressure pulses;
c. non-invasively measuring flow pulses in a central artery which supplies blood to the brain;
d. determining a central pressure pulse waveform that corresponds to the measured flow pulses;
e. calculating a pressure augmentation index from the central pressure pulse waveform;
f. calculating a flow augmentation index from the central flow pulse waveform; and
g. comparing the calculated pressure and flow augmentation indexes to measured pressure and flow augmentation data indicative of a measured ICP to thereby estimate actual ICP.

In one form, step a. includes measuring peripheral (radial) pressure pulses in a peripheral artery. In this form, step b. includes determining a peripheral pressure pulse waveform from the measured peripheral pulses and calculating the corresponding central pressure pulse waveform from the measured peripheral pressure pulse waveform, most preferably by using a transfer function. The peripheral pressure pulses are preferably measured in the radial artery at the wrist.

In an alternative form, step a. includes measuring carotid pressure pulses in a carotid artery. In this alternative form, step b. includes measuring the corresponding central pressure pulses, for example by applanation tonometry.

The flow pulses in step c. are preferably measured in an upper body artery which supplies blood to the brain, such as the internal carotid artery, anterior cerebral artery, middle cerebral artery or common carotid artery.

BRIEF DESCRIPTION OF THE DRAWINGS

A preferred embodiment of the invention will now be described, by way of an example only, with reference to the accompanying drawings, in which:

FIG. 3A is a graph of flow augmentation index % (FAIx) versus pressure augmentation index % (PAIx) for normal patient conditions. The relationship is linear.

FIG. 3B is a graph of flow augmentation index % (FAIx) versus pressure augmentation index % (PAIx), indicating the change in relationship (increase in PAIx and decrease in FAIx) for elevated ICP conditions. The relationship, at any given ICP condition, is again linear.

DETAILED DESCRIPTION OF THE PREFERRED EMBODIMENTS

Figure 1:
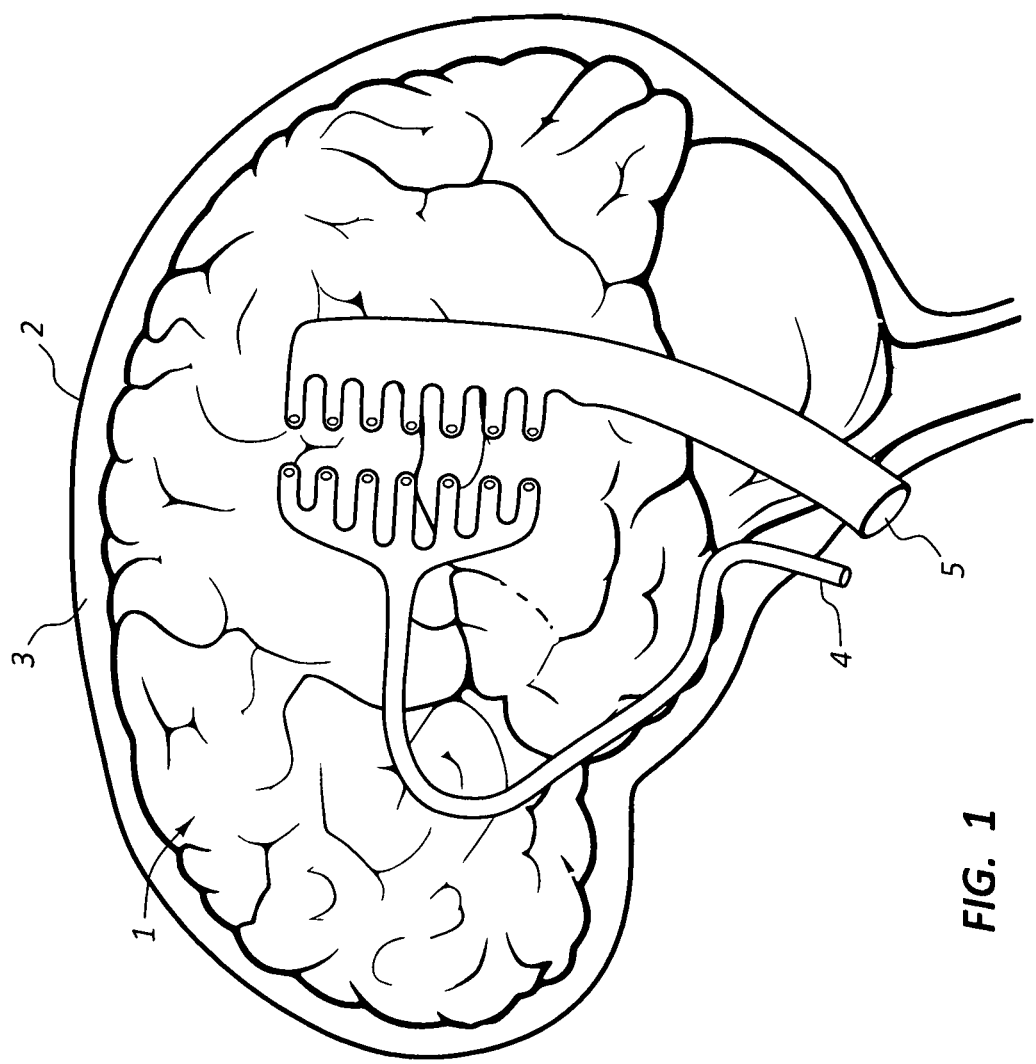
FIG. 1 is a schematic diagram showing the brain 1 within the cranium 2 with cerebrospinal fluid (CSF) 3 between brain 1 and cranium 2 and a cerebral artery 4 and jugular vein 5.
Figure 2B:
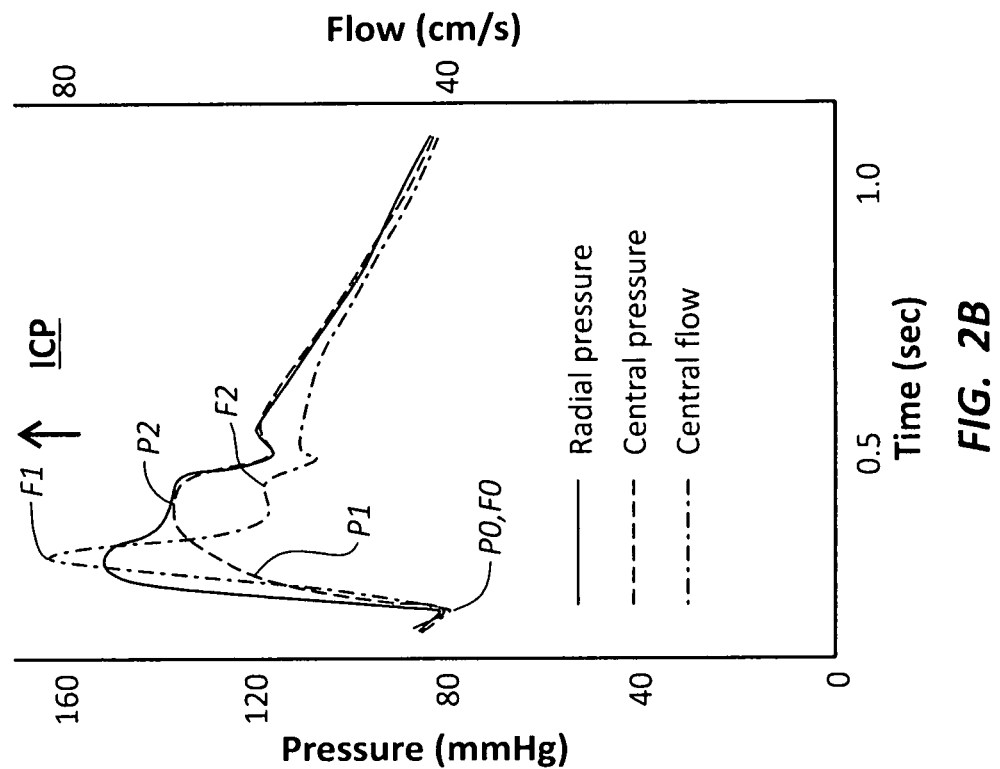
FIG. 2B is a graph showing peripheral (radial) arterial pressure (mm Hg) and central arterial pressure (mm Hg) and central arterial flow (cm/sec) versus time (sec) for elevated ICP patient conditions.
Figure 2A:
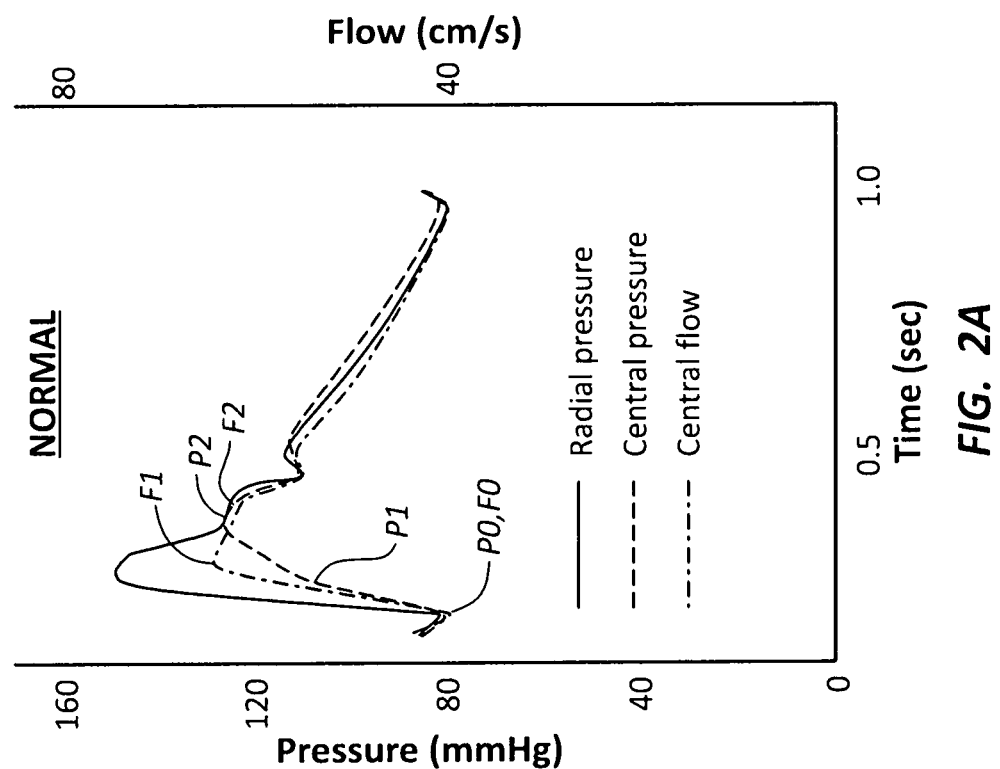
FIG. 2A is a graph showing peripheral (radial) arterial pressure (mm Hg) and central arterial pressure (mm Hg) and central arterial flow (cm/sec) versus time (sec) for normal (ie. non-elevated ICP) patient conditions.
Figure 4A:
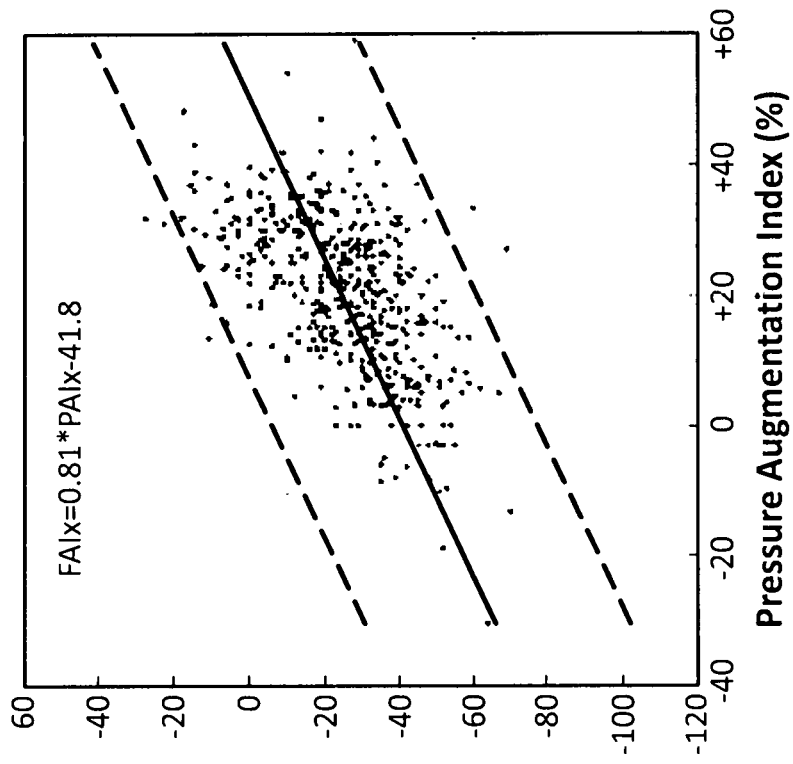
FIG. 4A is a graph of flow augmentation index % (FAIx) versus pressure augmentation index % (PAIx) for normal conditions, with actual data taken from a normal female population. Linear regression lines are shown at ±2 SD.
Figure 4B:
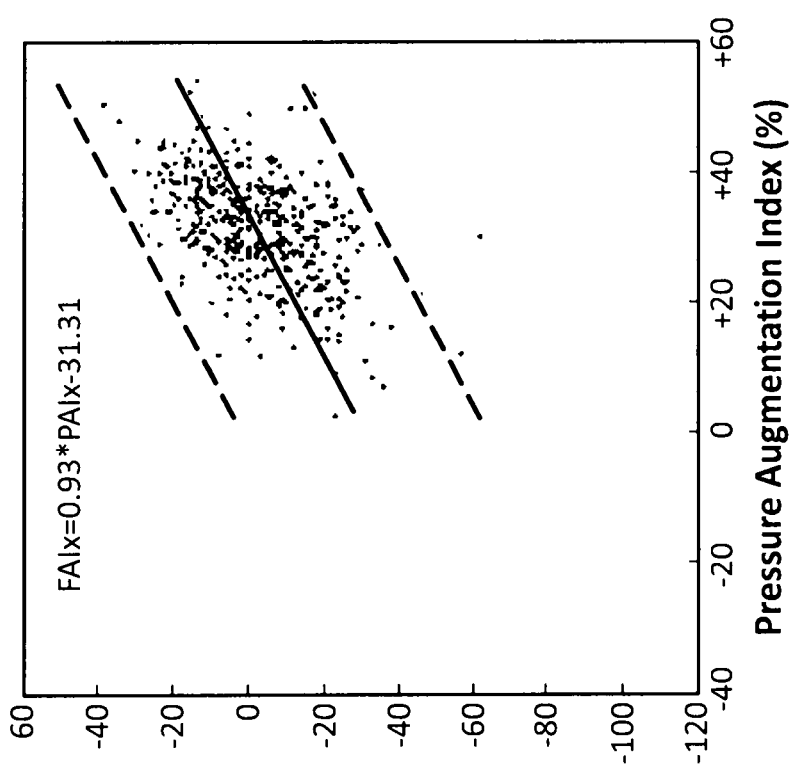
FIG. 4B is a graph of flow augmentation index % (FAIx) versus pressure augmentation index % (PAIx) for normal conditions, with actual data taken from a normal male population. Linear regression lines are shown at ±2 SD.

An embodiment of a method of non-invasively measuring ICP will now be described with reference to FIGS. 2A to 7B. The method comprises the steps of:

a. Measuring pressure pulses in a peripheral artery (typically the radial artery at the wrist, or the brachial artery) and producing an electrical pressure pulse waveform signal representing the measured peripheral pressure pulses. The measured peripheral pressure pulse waveform (specifically, radial pressure pulse waveform for measurements taken at the radial artery) is denoted in solid line in FIG. 2A for normal patient conditions and in solid line in FIG. 2B for elevated ICP conditions.

b. Deriving a Fourier transform for the measured peripheral pressure pulse waveform.

c. Deriving a Fourier transform associated with a central (central arterial) pressure pulse waveform by applying a transfer function $H(\omega)$ to the peripheral pressure pulse Fourier transform. The transfer function $H(\omega)$ being a transfer function relating a Fourier transform of pressure pulses in the peripheral artery and a Fourier transform of pressure pulses in a central artery, particularly the aorta.

d. Deriving the inverse of the Fourier transform associated with the central pressure pulse waveform, thereby producing an electrical signal representing a calculated central pressure pulse waveform. The calculated central pressure pulse waveform is denoted in black dashed line in FIG. 2A for normal patient conditions and in black dashed line in FIG. 2B for elevated ICP conditions. The above steps, method for determining features on the central pressure waveform, and calibration of peripheral (radial) pressures measured by radial tonometry to brachial cuff systolic and diastolic pressure are disclosed in U.S. Pat. No. 5,265,011 (the contents of which are incorporated herein by cross reference).

e. Determining the following features of the central pressure pulse waveform:
  i. The central arterial pressure at the point of systolic onset by taking a first derivative of the central pressure pulse waveform, and locating a zero crossing from negative-to-positive which precedes a maximum point on the first derivative curve, and designating this as P0.
  ii. A first localised systolic peak on the central pressure pulse waveform, within the limits of 60-140 msec from P0 (the foot of the pressure waveform), and designating this as P1.
  iii. A second localised systolic peak on the central pressure waveform, within the limits of 160-320 msec from P0 (the foot of the pressure waveform), and designating this as P2.
  iv. Peak pressure of pressure pulse waveform after P0 (the foot of the pressure pulse waveform), being the greater of P1 and P2.
  v. Pressure amplitude (PP).
  vi. Mean pressure (MP).
  vii. Pressure pulsatility index, wherein pressure pulsatility index is equal to pressure amplitude (PP) divided by mean pressure (MP).
  viii. Pressure augmentation (PA), wherein PA=P2−P1.
  ix. Pressure augmentation index (PAIx), wherein PAIx=PA÷(P2−P0) when P2>P1 and PAIx=PA÷(P1−P0) when P2<P1.

f. Non-invasively measuring flow pulses in a central artery supplying blood to the brain (typically common carotid, anterior cerebral, middle cerebral, basilar and/or, vertebral artery) by Doppler ultrasound technique, and producing an electrical signal representing the central flow pulse waveform. The measured central flow pulse waveform is denoted in black dashed-dotted line in FIG. 2A for normal patient conditions and in black dashed-dotted line in FIG. 2B for elevated ICP conditions.

g. Determining the following features of the central flow pulse waveform:
  i. Minimum flow velocity (F0).
  ii. A first localised systolic peak on the central flow pulse waveform within the limits of 60-140 msec from F0 (the foot of the central flow pulse waveform) and designating this as F1.
  iii. A second localised systolic peak on the central flow pulse wave form within the limits of 160-320 msec from F0 (the foot of the central flow pulse waveform) and designating this as F2
  iv. Peak flow velocity, being the greater of F1 and F2.
  v. Flow amplitude (FP), wherein flow amplitude=F1−F0 when F1>F0 and F2−F0 when F2>F1.
  vi. Mean flow velocity (MF), determined by integrating the central flow pulse waveform over one cardiac cycle.
  vii. Flow pulsatility index, wherein flow pulsatility index is equal to flow amplitude (FP) divided by mean flow (MP).
  viii. Flow augmentation (FA), wherein FA=F2−F1, designating flow augmentation as positive when F2>F1 and as negative when F2<F1.
  ix. Flow augmentation index (FAIx), wherein FAIx=FA flow amplitude (FP).

h. Determining flow/pressure augmentation index ratio, wherein the flow/pressure augmentation index ratio is equal to flow augmentation index (FAIx) divided by pressure augmentation index (FAIx). FIG. 3A shows a plot of the flow augmentation index (FAIx) versus pressure augmentation index (PAIx) for normal patient conditions, with FIG. 4A and FIG. 4B showing measured results for females and males respectively, whilst FIG. 3B shows plots of the flow augmentation index (FAIx) versus pressure augmentation index (PAIx) for various known (i.e. previously invasively measured) elevated ICP conditions.

i. Determining harmonic content of the central pressure and flow pulse waveforms by Fourier or frequency spectrum analysis.

j. Determining cerebral vascular impedance modulus (Z) as moduli of frequency components of the central pressure pulse waveform divided by corresponding moduli of frequency components of the central flow pulse waveform (see FIGS. 5A and 5B for normal patient and elevated ICP conditions respectively).

k. Determining cerebral vascular impedance phase ($\varphi$) as phase of frequency components of the central pressure pulse waveform minus corresponding phase of frequency components of the central flow pulse waveform (see FIGS. 6A and 6B for normal patient and elevated ICP conditions respectively).

l. Determining in-phase cerebral vascular impedance as cerebral vascular impedence modulus multiplied by the cosine of cerebral vascular impedance phase (Z cosine $\varphi$)(see FIGS. 7A and 7B for normal patient and elevated ICP conditions respectively).

m. Determining reflection coefficient as (ZT−ZC)÷(ZT+ZC), where ZT is terminal impedance modulus, being cerebral vascular impedence modulus at zero frequency (in dyne·s·cm−3) (estimated from the data in FIG. 5B) and ZC is characteristic impedance modulus, calculated as average value of cerebral vascular impedance modulus from frequency of second to sixth harmonics and after excluding values of pressure and flow in the noise level (P<0.4 mmHg), flow<1 cm/s) (again estimated from the data in FIG. 5B).

n. Determining ejection duration (ED) from the central pressure pulse wave form (EDp) and from the central flow pulse waveform (EDO (see FIG. 2B).

The measures determined are then compared to normal values for gender, age and heart rate to give an indication of ICP.

With reference to FIG. 3B, a clinician compares the calculated ICP pressure and flow augmentation indexes (represented as dots 18) to measured ICP augmentation index data (represented by the plots), which are indicative of a measured ICP, to thereby estimate actual ICP. The amount of actual elevated ICP is determined by selecting the known plot closest to the dots 18.

Figure 5B:
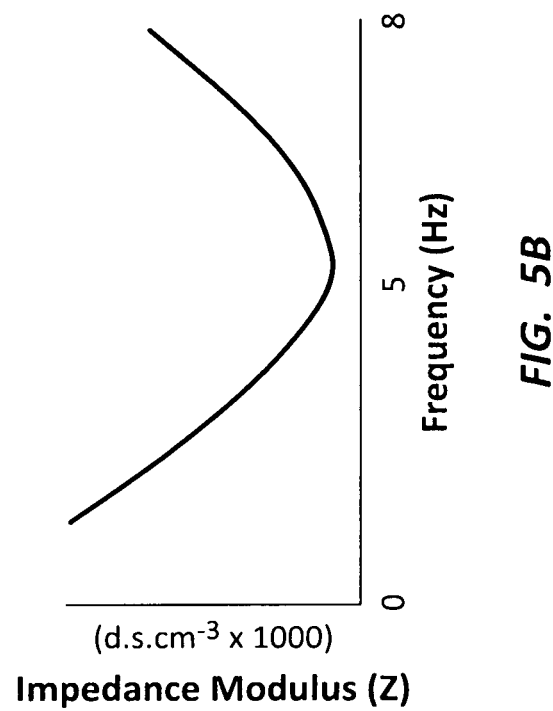
FIG. 5B is a graph of cerebral vascular impedance modulus (Z) (d·s·cm$^{-3}$×1000) versus frequency (Hz) for elevated ICP conditions.
Figure 5A:
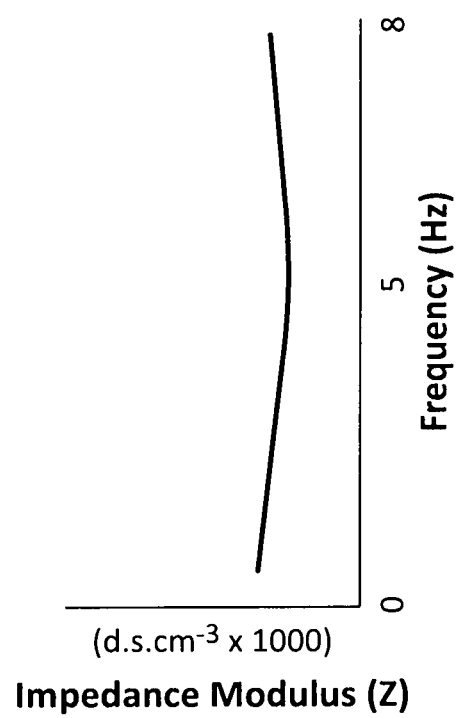
FIG. 5A is a graph of cerebral vascular impedance modulus (Z) (d·s·cm$^{-3}$×1000) versus frequency (Hz) for normal patient conditions.

The data shown in FIG. 5B is used to estimate characteristic impedance (ZC) and terminal impedance (ZT), and from these values, calculate reflection coefficient as (ZT−ZC)÷(ZT+ZC), as discussed above, as an indication of ICP.

Figure 6B:
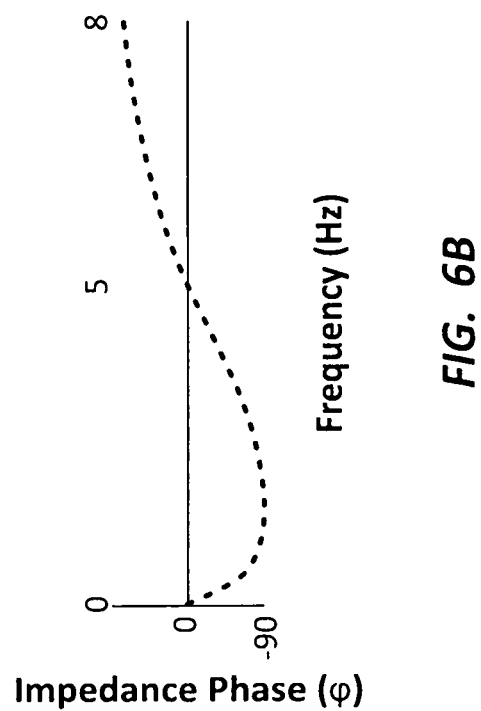
FIG. 6B is a graph of cerebral vascular impedance phase ($\varphi$) (degrees) versus frequency (Hz) for elevated ICP conditions.
Figure 6A:
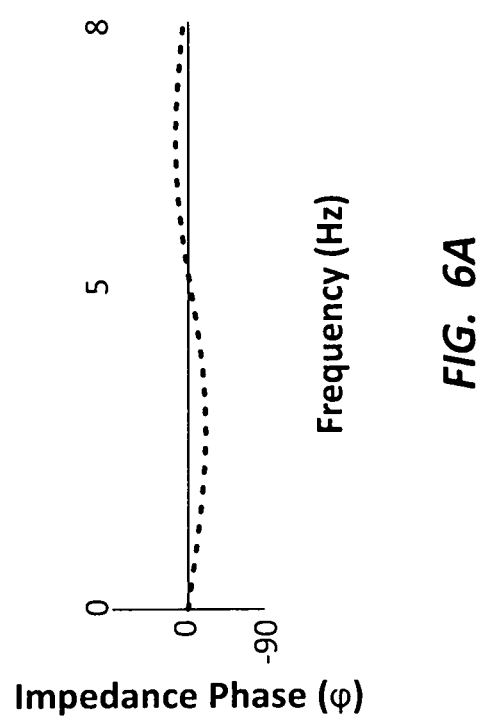
FIG. 6A is a graph of cerebral vascular impedance phase ($\varphi$) (degrees) versus frequency (Hz) for normal patient conditions.

The data shown in FIG. 6B, which shows the cerebral vascular impendence phase for the measured data, is compared against the data shown in FIG. 6A, which shows the cerebral vascular impedance phase under normal conditions. This is measured as average of phase delay over the same frequency band as used to estimate characteristic impedance, and with same criteria to exclude pressure and flow data in the noise level. This comparison of phase delay for the measured data against phase delay under normal conditions provides an indication of ICP.

Figure 7B:
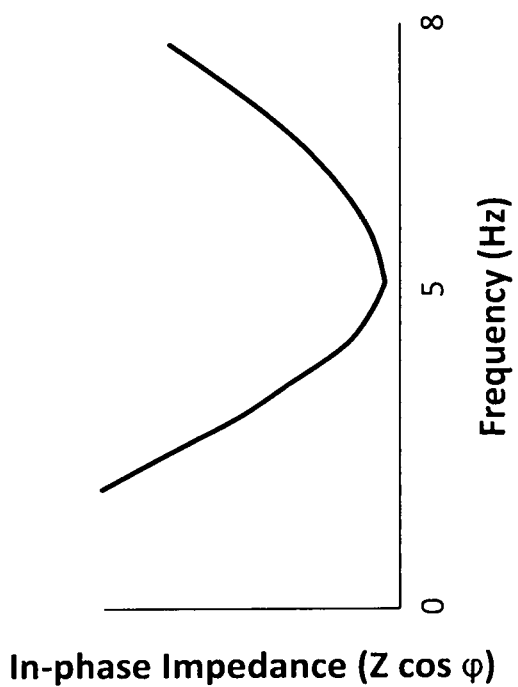
FIG. 7B is a graph of in phase cerebral vascular impedance (Z cosine $\varphi$) (degrees) versus frequency (Hz) for elevated ICP conditions.
Figure 7A:
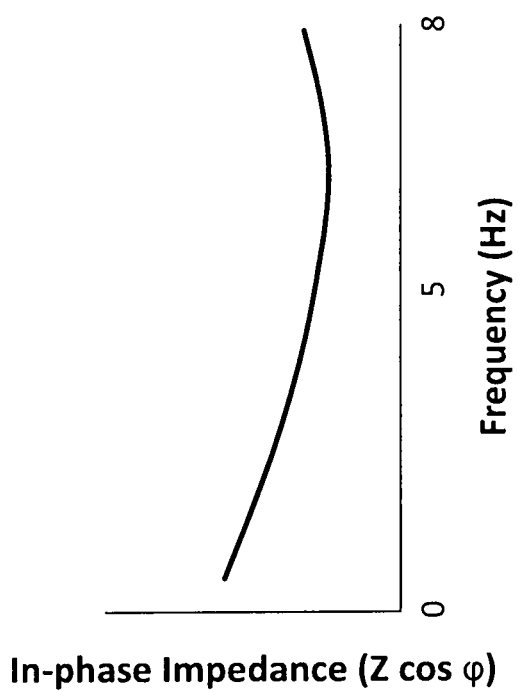
FIG. 7A is a graph of in phase cerebral vascular impedance (Z cosine $\varphi$) (degrees) versus frequency (Hz) for normal patient conditions.

The data shown in FIG. 7B is used to compare abnormal patterns of in-phase cerebral vascular impedance (Z cosine φ) fluctuations against normal non-fluctuant values of in-phase cerebral vascular impedance (Z cosine φ) (from FIG. 7A), by comparing average levels of in-phase cerebral vascular impedance (Z cosine φ) over the same frequency range that is used in FIG. 5B to calculate characteristic impedance, as described above. This comparison provides another indication of elevated ICP.

Ejection duration (ED) determined from the pressure pulse wave form (EDp) is compared to ED determined from the flow pulse waveform (EDf) as a check on the ability of the algorithm to identify left ventricular ED accurately and independently of reflected waves, with differences in determined ED giving an indication of elevated ICP.

The benefits of the non-invasive method of ICP measurement described above include:

no procedural risk of cerebral damage, haemorrhage and infection;

less requirement of direct measurement;

better discrimination in selecting patients for direct measurement;

more appropriate use of direct ICP measurement; and better management of patients without need for invasive measurement.

Although the invention has been described with reference to a preferred embodiment, it will be appreciated by those persons skilled in the art that the invention may be embodied in many other forms. For example, in an alternative embodiment (not shown), the pressure pulses are non-invasively measured in a central upper body artery, particularly the common carotid artery, rather than in a peripheral artery. In this embodiment, the central pressure pulses are directly measured, for example by applanation tonometry and the central pressure pulse waveform directly determined from the measured central pressure pulses.

The invention claimed is:

1. A non-invasive method of estimating intra-cranial pressure (ICP), the method being performed by a device, the device being selected from any one of a catheter, an applanation tonometry, and a Doppler ultrasound, the method comprising:
   a. measuring pressure pulses in an upper body artery;
   b. determining a central pressure pulse waveform that corresponds to the measured pressure pulses;
   c. non-invasively measuring flow pulses in a central artery which supplies blood to a brain;
   d. determining a central flow pulse waveform that corresponds to the measured flow pulses;
   e. determining ejection duration from the central pressure pulse waveform;
   f. determining ejection duration from the central flow pulse waveform; and
   g. determining a time difference between the ejection duration determined from the central pressure pulse waveform and the ejection duration determined from the central flow pulse waveform, wherein the time difference indicates an elevated ICP.

2. The method as claimed in claim 1, wherein step a. includes measuring peripheral pressure pulses in a peripheral artery.

3. The method as claimed in claim 2, wherein step b. includes sub-steps of:
   b1. determining a peripheral pressure pulse waveform from the measured peripheral pulses; and
   b2. calculating a corresponding central pressure pulse waveform from the peripheral pressure pulse waveform.

4. The method as claimed in claim 3, wherein the calculating of the corresponding central pressure pulse waveform from the peripheral pressure pulse waveform is done using a transfer function.

5. The method as claimed in claim 3, wherein the peripheral pressure pulses are measured in a radial artery at a wrist.

6. The method as claimed in claim 1, wherein step a. includes non-invasively measuring carotid pressure pulses in a carotid artery.

7. The method as claimed in claim 1, wherein step a. includes non-invasively measuring central pressure pulses in an upper body central artery.

8. The method as claimed in claim 7, wherein the central pressure pulses are measured by applanation tonometry.

9. The method as claimed in claim 1, wherein the flow pulses in step c. are measured in the upper body artery which supplies blood to the brain.

10. The method of claim 1, wherein step a. includes measuring the pressure pulses non-invasively.

11. The method of claim 1 further comprising: determining harmonic content of the central pressure pulse waveform and central flow pulse waveform;
   determining cerebral vascular impedance modulus data from the determined harmonic content; and
   comparing the determined cerebral vascular impedance modulus data to measured cerebral vascular modulus data indicative of a measured ICP to provide an indication of actual ICP.

12. The method of claim 1 further comprising: determining harmonic content of the central pressure pulse waveform and central flow pulse waveform; determining cerebral vascular impedance phase data from the determined harmonic content; and comparing the determined cerebral vascular impedance phase data to measured cerebral vascular phase data indicative of a measured ICP to provide an indication of actual ICP.

13. The method of claim 1 further comprising: determining harmonic content of the central pressure pulse waveform and central flow pulse waveform;

determining cerebral vascular impedance modulus data from the determined harmonic content;

determining cerebral vascular impedance phase data from the determined harmonic content;

determining in-phase cerebral vascular impedance data from the determined cerebral vascular impendence modulus data and determined cerebral vascular impedance phase data; and comparing the determined in-phase cerebral vascular impedance data to measured in-phase cerebral vascular impedance data indicative of a measured ICP to provide an indication of actual ICP.

* * * * *